United States Patent [19]

Friedlander et al.

[11] Patent Number: 5,545,655

[45] Date of Patent: *Aug. 13, 1996

[54] SUBSTITUTED OXATHIOLANES

[75] Inventors: Barry T. Friedlander, Guelph, Canada; Robert A. Davis; Allen R. Blem, both of Cheshire, Conn.; David L. Walker, Waterloo, Canada

[73] Assignees: Uniroyal Chemical Company, Inc., Middlebury, Conn.; Uniroyal Chemical Ltd./Ltee, Elmira, Canada

[ * ] Notice: The term of this patent shall not extend beyond the expiration date of Pat. No. 4,870,094.

[21] Appl. No.: 344,395

[22] Filed: Nov. 23, 1994

Related U.S. Application Data

[63] Continuation of Ser. No. 202,850, Feb. 25, 1994, abandoned, which is a continuation of Ser. No. 81,904, Jun. 23, 1993, abandoned, which is a continuation of Ser. No. 720,050, Jul. 16, 1991, abandoned, which is a division of Ser. No. 291,381, Dec. 23, 1988, Pat. No. 5,039,332, which is a continuation of Ser. No. 777,910, Sep. 19, 1985, abandoned.

[51] Int. Cl.⁶ .......................... A01N 43/50; A01N 43/28; C07D 405/00; C07D 409/06
[52] U.S. Cl. .......................... 514/397; 514/211; 514/212; 514/228.8; 514/232.2; 514/235.5; 514/235.8; 514/316; 514/318; 514/326; 514/341; 540/467; 540/544; 540/597; 540/603; 544/96; 544/124; 544/129; 544/139; 546/187; 546/193; 546/210; 546/228; 546/272.4; 546/272.7
[58] Field of Search ...................... 540/467, 544, 540/597, 603; 544/96, 124, 129, 139; 546/187, 193, 210, 228, 316; 548/311.1; 514/211, 212, 228.8, 232.2, 235.5, 235.8, 316, 318, 326, 341, 397

[56] References Cited

U.S. PATENT DOCUMENTS

| | | | |
|---|---|---|---|
| 3,829,437 | 8/1974 | Zumach et al. | 549/30 |
| 4,150,153 | 4/1979 | Walker | 548/336 |
| 4,423,057 | 12/1983 | Walker | 548/336 |
| 4,524,110 | 6/1985 | Heeres et al. | 548/336 |
| 4,542,130 | 9/1985 | Weissmuller et al. | 514/212 |
| 4,559,355 | 12/1985 | Krantz et al. | 548/336 |
| 4,870,094 | 9/1989 | Friedlander et al. | 548/336 |

FOREIGN PATENT DOCUMENTS 2027701  2/1980  United Kingdom.

*Primary Examiner*—Patricia L. Morris
*Attorney, Agent, or Firm*—Raymond D. Thompson

[57] ABSTRACT

This invention relates to novel imidazole and triazole substituted oxathiolane compounds and compositions containing said compounds having fungicidal and plant growth regulant activity and methods for preparing same.

14 Claims, No Drawings

SUBSTITUTED OXATHIOLANES

This is a continuation of prior complete application U.S. Application Ser. No. 08/202,850 filed Feb. 25th, 1994, now abandoned, which is a continuation of prior complete application U.S. Ser. No. 08/081,904 filed Jun. 23, 1993, now abandoned, which is a continuation of application Ser. No. 07/720,050 filed Jul. 16, 1991, now abandoned, which application is a division of Ser. No. 07/291,381 filed Dec. 23, 1988, issued on Aug. 13, 1991 as U.S. Pat. No. 5,039,332 which is a continuation of application Ser. No. 06/777,910, filed Sep. 19, 1985, now abandoned.

BACKGROUND OF THE INVENTION

1. Field of the Invention

This invention relates to novel imidazole and triazole substituted oxathiolane compounds having fungicide and plant growth regulant activity and methods for preparing same.

2. Description of the Prior Art

As a result of the economic loss which accompanies fungicidal attack on plants, especially crops, there is a constant need for new broad spectrum fungicides.

Moreover, the need for agricultural chemicals having significant effects on the growth and development of crop plant species is similarly well known. Thus, for many crops, it is highly desirable that certain plant growth regulatory effects be accomplished. In general, these growth regulatory effects include one or more of the following: dwarfing, cessation of terminal growth, inhibition or stimulation of axillary and intercalary growth, retardation or stimulation of internode elongation, inhibition or stimulation of flowering or reproductive development, and the like. Of particular interest is the growth retardancy of such important commercial crops as soy bean, cotton, bean and cereal grains, including barley.

Among the many classes and types of compounds developed for antimicrobial use are the various classes of imidazole and triazole dithiolanes as exemplified in (U.S.P.) U.S. Pat. No. 4,483,865, U.S. Pat. No. 4,359,475 and European Patent Publication (EPO) 0,061,789 and dioxolanes as taught in U.S. Pat. Nos. 4,160,838, 3,575,999, 4,402,963, 4,079,062, Australian Patent A-86640/82 and J. Med. Chem. 12,784 (1969).

SUMMARY OF THE INVENTION

The instant invention is directed to a new class of imidazole or triazole substituted compounds whose activity against a wide spectrum of fungi is greater than the imidazole or triazole substituted compounds of the prior art and which provides a new aid in plant growth regulant technology.

In accordance with this invention, said compounds are set forth by the following general formula:

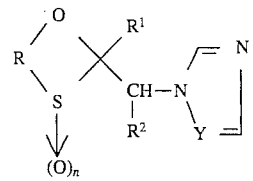

wherein

R is $C_2$–$C_4$ alkylene unsubstituted or substituted with $C_1$–$C_{10}$ alkyl, alkenyl, alkynyl or alkoxyalkyl;

$R^1$ is (a) $C_5$–$C_8$ bridged or non-bridged cycloalkyl or cycloalkenyl;

(b) phenyl, methylenedioxyphenyl, naphthyl, pyridyl, furanyl or thienyl; the (b) substituents being unsubstituted or substituted with:

$C_1$–$C_{10}$ alkyl, OH, SH, cyclohexyl, $C_1$–$C_{10}$ haloalkyl, $C_1$–$C_{10}$ alkenyl, cyano, nitro, $XR^3$ or a single halogen wherein X is O, S, SO or $SO_2$ and $R^3$ is $C_1$–$C_{10}$ alkyl, $C_1$–$C_{10}$ alkenyl, $C_1$–$C_{10}$ alkoxyalkyl, $C_1$–$C_6$ haloalkyl, $C_1$–$C_6$ haloalkenyl, $C_5$–$C_6$ cycloalkyl, $C_7$–$C_9$ aralkyl;

$C_1$–$C_4$ alkylsulfonyloxy, phenylsulfonyloxy,

wherein $R^4$ is $C_1$–$C_4$ alkyl or phenyl;

wherein $R^5$ and $R^6$ are individually H, $C_1$–$C_4$ alkyl or phenyl with the proviso that $R^5$ and $R^6$ are not both H;

$NR^7R^8$ wherein $R^7$ and $R^8$ are individually H or $C_1$–$C_4$ alkyl, $R^7$ is H, $R^8$ is $COR^9$, $COOR^9$ or $SO_2R^9$ wherein $R^9$ is $C_1$–$C_4$ alkyl or phenyl, or $R^7$ and $R^8$ together form $C_4$–$C_6$ alkylene, $C_4$–$C_6$ oxydialkylene or phenylmethylene;

$R^2$ is H or $C_1$–$C_6$ alkyl;

Y is N or CH; and n is 0, 1 or 2; and the physiologically acceptable addition salts thereof.

The instant invention is furthermore directed to a process for controlling fungi by the application of a fungicidally effective amount of a compound within the above generic formula.

The invention is still further characterized by a fungicidal composition which comprises a compound as recited above with a carrier therefor.

Finally, the instant invention is directed to a plant growth regulant composition comprising a compound of the instant invention and a carrier therefor. Also, the instant invention is directed to a method for regulating plant growth by employing the plant growth composition of this invention.

DETAILED DESCRIPTION OF THE INVENTION

This invention relates to compounds of the following generic formula I:

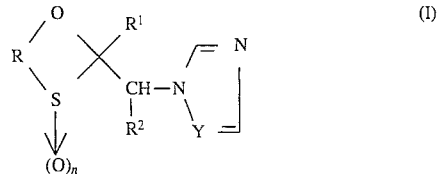

wherein R is $C_2$–$C_4$ alkylene unsubstituted or substituted with $C_1$–$C_{10}$ alkyl, alkenyl, alkynyl or alkoxyalkyl;

$R^1$ is
 (a) $C_5$–$C_8$ bridged or non-bridged cycloalkyl or cycloalkenyl;
 (b) phenyl, methylenedioxyphenyl, naphthyl, pyridyl, furanyl or thienyl; the (b) substituents being unsubstituted or substituted with:
  $C_1$–$C_{10}$ alkyl, OH, SH, cyclohexyl, $C_1$–$C_{10}$ haloalkyl, $C_1$–$C_{10}$ alkenyl, cyano, nitro, $XR^3$ or a single halogen wherein
   X is O, S, SO or $SO_2$ and
   $R^3$ is $C_1$–$C_{10}$ alkyl, $C_1$–$C_{10}$ alkenyl, $C_1$–$C_{10}$ alkoxyalkyl, $C_1$–$C_6$ haloalkyl, $C_1$–$C_6$ haloalkenyl, $C_5$–$C_6$ cycloalkyl, $C_7$–$C_9$ aralkyl;
  $C_1$–$C_4$ alkylsulfonyloxy, phenylsulfonyloxy,

wherein $R^4$ is $C_1$–$C_4$ alkyl or phenyl;

wherein $R^5$ and $R^6$ are individually H, $C_1$–$C_4$ alkyl or phenyl with the proviso that $R^5$ and $R^6$ are not both H;
wherein $R^7$ and $R^8$ are individually H or $C_1$–$C_4$ alkyl, $R^7$ is H, $R^8$ is $COR^9$ $COOR^9$ or $SO_2R^9$
wherein $R^9$ is $C_1$–$C_4$ alkyl or phenyl, or
$R^7$ and $R^8$ together form $C_4$–$C_6$ alkylene, $C_4$–$C_6$ oxydialkylene or phenylmethylene;
$R^2$ is H or $C_1$–$C_6$ alkyl;
Y is N or CH; and
n is 0, 1 or 2; and the physiologically acceptable addition salts thereof.

The compounds of formula I contain an asymmetric carbon atom at the 2-position of the oxathiolane ring which results in the existence of optical isomers. These isomers and their mixtures are within the scope of this invention.

Preferred compounds of this invention are those according to formula I wherein
R is $C_2$ alkylene unsubstituted or substituted with $C_1$–$C_3$ alkyl;
$R^1$ is
 (a) $C_5$–$C_6$ cycloalkyl;
 (b) unsubstituted phenyl, naphthyl, thienyl; phenyl or thienyl substituted with F, Cl, Br, $C_1$–$C_7$ alkyl, $XR^3$ wherein X is O, S, SO or $SO_2$ and
  $R^3$ is $C_1$–$C_7$ alkyl, cyclohexyl; methylsulfonyloxy, phenylsulfonyloxy, dimethylaminocarbonyloxy or $NR^7R^8$
  wherein $R^7$ and $R^8$ are individually H or $C_1$–$C_2$ alkyl
  $R^7$ and $R^8$ together are phenylmethylene and
  where $R^7$ is H, $R^8$ is methylsulfonyl, phenylsulfonyl or $C_1$–$C_4$ alkyoxycarbonyl;
$R^2$ is H;
Y is N or CH; and
n is 0, 1 or 2.

More preferred compounds of this invention are those of formula I wherein
R is $C_2$ alkylene unsubstituted or substituted with $C_1$–$C_3$ alkyl;
$R^1$ is
(a) cyclohexyl;
(b) unsubstituted phenyl, naphthyl, thienyl;
phenyl or thienyl substituted with F, Cl, Br, $C_1$–$C_7$ alkyl or $C_2$–$C_7$ alkoxy;
$R^2$ is H;
Y is N or CH; and
n is 0, 1 or 2.

Most preferred compound of this invention are those of formula I wherein
R is $C_2$ alkylene unsubstituted or substituted with $C_1$–$C_3$ alkyl;
$R^1$ is
(a) cyclohexyl;
(b) phenyl or thienyl substituted with F, Cl, Br, $C_1$–$C_7$ alkyl or $C_2$–$C_7$ alkoxy;
$R^2$ is H;
Y is N or CH; and
n is 0, 1 or 2.

The compounds of this invention have particular application as fungicides in the control of fungus growth on plants and vegetation. It is particularly noteworthy that the compounds of this invention are effective against phytopathogenic fungi which are systemic in the plant or deeply embedded in plant tissue. Among these classes of fungi which are effectively controlled by the compounds of this invention is powdery mildew disease in barley (*Erysiphe graminis*) and cucumber (*Erysiphe cichoracearum*) and rust diseases such as bean rust (*Uromyces phaseoli*). Certain compounds of this invention have also demonstrated effectiveness against other fungi which cause plant disease, including, for example, *Alternaria solani, Cercospora arachidicola, Phytophthora infestans, Sclerotinia sclerotiorum, Sclerotium rolfsii, Fusarium oxysporum, Helminthosporium maydis* and *Piricularia oryzae*.

The compounds of this invention can be prepared by catalytic reaction of azole-substituted ketones with mercapto-alcohols and the subsequent cyclization of the intermediate so formed.

Azole-substituted ketones may be prepared from haloketones by substitution of the halogen atom with an azole (imidazole or 1H-1,2,4-triazole) by methods disclosed in Canadian Patent No. 1,054,613 and French Patent No. 2,303,475.

Conversion of azole-substituted ketones to compounds of this invention where n=0 is accomplished by reaction of the azoleketone with a mercaptoalcohol. At least one mole, and preferably an excess of mercaptoalcohol is required for the cyclization for which an acid catalyst is necessary, preferably p-toluenesulfonic acid. The cyclization is preferably carried out in a solvent mixture such as toluene and 1-butanol and is accompanied by azeotropic removal of water.

Sulfoxides and sulfones are obtained by oxidation of compounds where n=0 with hydrogen peroxides or organic hydroperoxides such as m-chloroperoxybenzoic acid in a chlorinated hydrocarbon solvent, preferably dichloromethane or chloroform. Sulfoxides may specifically be formed by reaction of oxathiolanes with one equivalent of m-chloroperoxybenzoic acid at between 0° C. and ambient temperature-. Conversion of oxathiolanes to sulfones may be carried out by reaction with at least two equivalents and preferably an excess of m-chloroperoxybenzoic acid in a chlorinated hydrocarbon solvent at the reflux temperature of the solvent.

Compounds of formula I where R is substituted ethylene (—$CH_2$—$CH(R^*)$—) may be separately synthesized as either of two isomeric compounds where substitution of the alkyl substituent $R^*$ is either at the 4-position or the 5-position of the oxathiolane ring.

In order to effectively employ the compounds of this invention in their prime use, as fungicides, the compounds may be applied neat or in admixture with inert carriers and/or additives to form fungicidally effective compositions. In one such embodiment, the compound is combined with a solid inert carrier. Among the inert carriers within the contemplation of this invention, are the mineral silicates, e.g., mica, talc, pyrophylite and the clays. Other solid carriers, within the contemplation of this invention, include vermiculite, charcoal and corn cobs. Solid compositions made by combining the inert carriers recited above with the active compound are applied by well-known methods in the art such as broadcasting, side dressing, soil incorporation and seed treatment.

In another preferred embodiment of this invention, a liquid composition comprising an active compound and a liquid inert carrier is employed. In this embodiment, the liquid carrier may be a solvent or a suspending agent for the active compound of this invention. It is emphasized that the carrier itself is inert in terms of providing fungicidal activity.

Among the liquid carriers within the contemplation of this invention are water, alkanols and aromatic solvents such as substituted and unsubstituted phenol, benzene, kerosene, toluene and xylene.

Another preferred embodiment of the liquid composition is an emulsion formed by dissolving an active compound of this invention in a suitable organic solvent and then adding the solvent to water. Of course, a suitable emulsifying agent, such as a surface active agent which may be anionic, non-ionic or cationic, is added in the formation of the emulsion.

In yet another embodiment of the liquid composition, an active compound of this invention is combined with water to form a dispersion in the absence of an organic solvent. Again, surface-active dispersing agents are employed in the preparation of the suspension.

The surface-active agents effective in the preparation of liquid compositions are known to the art. For example, U.S. Pat. No. 2,547,734 provides detailed examples of such agents employed in emulsions and dispersions.

In yet another liquid composition embodiment, solutions are prepared for aerosol application of a compound of this invention. These compositions are prepared by dissolving the active compound directly in an aerosol solvent which is a liquid at elevated pressures. The aerosol method involves releasing the aerosol solution in the atmosphere at a pressure at which the carrier is a gas. Alternatively, the aerosol solution may be prepared by first dissolving an active compound of this invention in a less volatile solvent and then admixing the thus formed solution with a highly volatile liquid aerosol carrier and proceeding as discussed above.

In another embodiment, a two-phase composition is provided. In this application, an active compound of this invention is first absorbed on the surface of an inert solid carrier. As stated above, the various mineral silicates are particularly preferred in this application. These inert silicates are then dispersed, in the presence of a dispersing agent, in a suitable non-solvent medium, usually water.

Illustrative, non-limiting examples of suitable solvents which may be used in the application of the microbiocides of this invention are acetone, methanol, isopropanol, t-butyl alcohol, cyclohexanol, cyclohexanone, n-butyl alcohol, toluene, xylene, dioxane, dimethyl formamide, dimethylsulfoxide, ethylene dichloride, diacetone alcohol, and n-methyl pyrrolidone. Water emulsions prepared from these solutions may also be applied to the locus under attack by microbes.

The microbiocides of this invention can be applied foliarly to the plant to be protected or to the soil in which the plants to be protected are grown. If applied foliarly, the concentration of the active ingredient is applied at a rate of from about 0.125 to about 10.0 kilograms per hectare (kg/ha). More preferably, the rate of foliar application is in the range of between 0.125 and 5.0 kg/ha. Those skilled in the art will appreciate that the exact concentration depends greatly on the disease being controlled and the crop being protected.

In the embodiment wherein protection is provided by application of the active ingredient to the soil, the dosage rate is from about 5 to 500 parts per million (ppm) of active ingredient. The particular dosage within this range again depends on the disease being controlled and the crop being protected. In the microbiocidal use of the active compounds of this invention, the application of the active may be applied prior to any infection or after a microbe attack has begun.

In still another application of the microbiocidal use of the compound of this invention, the active is applied to seeds as a coating. This method accomplishes the same purpose as is provided by protecting the plant chemotherapeutically or systemically by absorbing the active into the plant. When the microbiocidal use is as a coating to seeds, the appropriate dosage is in the range of from about 5 to 75 grams of active per hundred kilograms of seed.

In yet another aspect of this invention, a process is provided for regulating plant growth which includes the application of a compound of this invention as a plant growth regulant. In this process, the active ingredient is preferably applied foliarly. As in the case of the microbiocidal use of the active ingredient, the compound is applied as a liquid, either as an organic solution, or as a water emulsion. Most preferably, the plant growth regulant is applied as a water emulsion, suspension or solution.

In the use of a compound of this invention as a plant growth regulant, the dosage applied is in the range of from about 0.125 to about 10.0 kilograms of active ingredient per hectare (kg/ha). More preferably, the concentration of active as a plant growth regulant is in the range of from about 0.125 to about 5.0 kg/ha. It is preferred that the application as a plant growth regulant be as an atomized spray or as a soil treatment.

The most suitable dosage and method of application of the active ingredient(s) for plant growth regulatory effects and the type and amount of adjuvant substances to be added to the spray solution will depend on a number of factors, including the plant species; the stage of plant development; the mode of application; the specific biological effect desired; the air and soil temperature; the quantity and intensity of rainfall before and after treatment; the soil type, pH, fertility and moisture and organic matter content; the physiological condition and vigor of the target plants; the relative humidity and wind velocity of the air around the crop; the extent and density of the foliar canopy of the target plant; the light quality, intensity and duration each day; the type and interval of previous and subsequent crop protectant chemical applications. All of these factors may have an influence on the efficacy of chemicals applied as plant growth regulators. However, one skilled in the art can, by routine experimentation, readily determine optimum conditions for the employment of any particular compound of this invention.

The following examples are given to illustrate this invention and no express or implied limitation of the invention to these examples is intended.

EXAMPLE 1

1-[ (2-phenyl-1,3-oxathiolan-2-yl)methyl]-1 H-1,2,4-triazole (Cpd. No. 1)

To a solution of 5.6 g 1-phenyl-2-1H-1,2,4-triazol- 1-yl)ethanone and 4.7 g 2-mercaptoethanol in 100 ml dry toluene and 50 ml 1-butanol was added with stirring 7.6 g p-toluenesulfonic acid, which resulted in the formation of a slurry. The mixture was refluxed under a Dean-Stark trap for about 40 hours, until no more water collected. The solvent was evaporated, the residue taken up in dichloromethane and washed twice with 10% aqueous sodium hydroxide and once with water. The solution was dried, filtered and evaporated leaving a solid which was recrystallized from toluene/petroleum ether to give 4.6 g of product.

EXAMPLE 2

1-[[2-(4-methoxyphenyl)-1,3-oxathiolan-2-yl]methyl]-1 H- 1,2,4-triazole (Cpd. No. 22)

To a slurry of 32.5 g 1-(4-methoxyphenyl)-2-(1H- 1,2,4-triazole-1-yl) ethanone in 500 ml dry toluene and 250 ml 1-butanol was added 23.4 g 2-mercaptoethanol and 38.0 g p-toluenesulfonic acid. The thickened slurry was refluxed under a Dean-Stark trap for about 40 hours, until no more water collected. The solvent was evaporated leaving a solid residue which was dissolved in dichloromethane and washed twice with 10% aqueous sodium hydroxide and once with water. The organic layer was dried, filtered and evaporated to leave an oily residue which partially solidified on high vacuum pumping. The residue was triturated with hot toluene/cyclohexane, cooled and filtered to give 6.5 g of product.

EXAMPLE 3

1-[ [2-(4-chlorophenyl)-1,3-oxathiolan-2-yl]methyl]-1 H- 1,2,4-triazole (Cpd. No. 6)

To a slurry of 44.3 g 1-(4-chlorophenyl)-2-(1H- 1,2,4-triazol-1-yl) ethanone in 800 ml dry toluene and 400 ml 1-butanol was added 31.2 g 2-mercaptoethanol and 51.0 g p-toluenesulfonic acid. The mixture was refluxed under a Dean-Stark trap for 48 hours. On cooling, a white solid precipitated out, which was removed by filtration. The filtrate was evaporated, the residue dissolved in dichloromethane and washed twice with 10% aqueous sodium hydroxide and once with water. The organic layer was dried, filtered and evaporated to leave an oil which was taken up in cyclohexane. The cyclohexane was evaporated to azeotrope off any remaining 1-butanol, leaving an oily solid which was triturated with petroleum ether to give 15.7 g of product.

EXAMPLE 4

1-[[2-(4-bromophenyl)-1,3-oxathiolan-2-yl]methyl]-1 H- 1,2,4-triazole (Cpd. No. 9)

To a slurry of 27.8 g 1-(4-bromophenyl)-2-(1 H-1,2,4-triazol- 1-yl) ethanone in 350 ml dry toluene and 175 ml 1-butanol were added 15.6 g 2-mercaptoethanol and 24.7 g p-toluenesulfonic acid. The mixture was refluxed under a Dean-Stark trap for 50 hours. After cooling, a white solid was removed by filtration and the filtrate evaporated. The residue was taken up in chloroform and washed twice with 10% aqueous sodium hydroxide and once with water. The organic layer was dried, filtered and evaporated to leave a liquid residue. The 1-butanol in the residue was removed azeotropically three times with cyclohexane leaving a slurry. The solid was isolated by filtration to give 5.2 g of product.

EXAMPLE 5

1[[2-(4-chlorophenyl)-1,3-oxathiolan-2-yl]methyl]-1 H- 1,2,4-triazole S-oxide (Cpd. No. 7)

To a solution of 6.7 g 1-[[2-(4-chlorophenyl)-1,3-oxathiolan- 2-yl]methyl]-1H-1,2,4-triazole in 60 ml dichloromethane was added dropwise 4.9 g of 80–85% m-chloroperoxybenzoic acid in 50 ml dichloromethane at 0° C. After the addition was complete, the reaction mixture was allowed to warm to room temperature and was stirred overnight. The solution was washed twice with 5% aqueous sodium bicarbonate, once with water, dried and evaporated leaving a sticky yellow solid. The product was triturated with ether to leave as a white powder 3.8 g of product.

EXAMPLE 6

1-[[2-(4-chlorophenyl)-1,3-oxathiolan-2-yl]methyl]-1 H- 1,2,4-triazole S,S-dioxide (Cpd. No. 8)

To a solution of 5.6 g 1-[[2-(4-chlorophenyl)-1,3-oxathiolan- 2-yl]methyl]-1H-1,2,4-triazole in 90 ml dichloromethane was added dropwise 10.1 g m-chloroperoxybenzoic acid in 175 ml dichloromethane at room temperature. After the addition was complete, the reaction mixture was refluxed for 18 hours. The volume was then reduced by one-half and the resulting precipitate was removed by filtration. The filtrate was washed twice with 5% aqueous sodium bicarbonate, once with water, dried and evaporated to leave a sticky solid. Recrystallization of this solid from toluene/petroleum ether gave 3.4 g of product.

Additional compounds were prepared following procedures similar to those set forth in Examples 1 through 6.

TABLE I

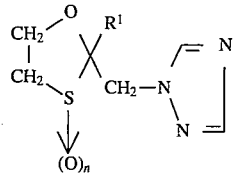

| Cpd. No. | R¹ | n | m.p. (°C.) |
|---|---|---|---|
| 1 | 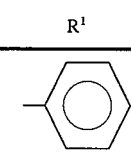 | 0 | 100–102 |
| 2 | " | 1 | 100–112 |
| 3 | " | 2 | 121–125 |
| 4 | 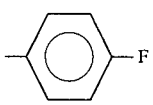 | 0 | 117–118 |
| 5 | " | 2 | 173–175 |

TABLE I-continued structure: CH₂-O-C(R¹)(CH₂-N(N=CH-CH=N ring))-CH₂-S(O)ₙ (oxathiolane with triazole)

| Cpd. No. | R¹ | n | m.p. (°C.) |
|---|---|---|---|
| 6 | 4-Cl-C₆H₄ | 0 | 110–112 |
| 7 | 4-Cl-C₆H₄ | 1 | 125–130 |
| 8 | " | 2 | 155–160 |
| 9 | 4-Br-C₆H₄ | 0 | 122–124 |
| 10 | 4-Br-C₆H₄ | 2 | 144–148 |
| 11 | 4-CH₃-C₆H₄ | 0 | 114–117 |
| 12 | " | 2 | 135–140 |
| 13 | 4-(CH₂-CH₂-CH₃)-C₆H₄ | 0 | 40–42 |
| 14 | 4-CH(CH₃)₂-C₆H₄ | 0 | 66–68 |
| 15 | 4-C(CH₃)₃-C₆H₄ | 0 | 105–106 |
| 16 | " | 2 | 153–155 |
| 17 | 4-(tetrahydrothiopyranyl)-C₆H₄ | 0 | 88–90 |
| 18 | " | 2 | 155–157 |
| 19 | 3-HO-C₆H₄ | 0 | 186–188 |
| 20 | 4-OH-C₆H₄ | 0 | 96–100 |
| 21 | 4-OH-C₆H₄ | 2 | 185–187 |
| 22 | 4-OCH₃-C₆H₄ | 0 | 145–155 |
| 23 | " | 2 | 65–70 |
| 24 | 4-O-CH(CH₃)₂-C₆H₄ | 0 | 78–79 |
| 25 | " | 1 | 134–135 |
| 26 | " | 2 | 138–139 |
| 27⁽¹⁾ | 4-O-(CH₂)₄-CH₃-C₆H₄ | 0 | Oil |
| 28 | " | 2 | 128–129 |
| 29⁽¹⁾ | 4-O-(CH₂)₄-CH₃-C₆H₄ | 0 | Oil |
| 30 | 2-(CH₃-CH₂-O)-C₆H₄ | 0 | 73–75 |
| 31 | 2-(CH₃-CH(CH₃)-O)-C₆H₄ | 0 | 97–99 |
| 32 | 2-(CH₃-(CH₂)₄-O)-C₆H₄ | 0 | 68–70 |
| 33⁽¹⁾ | 2-(CH₃-(CH₂)₄-O)-C₆H₄ | 2 | Oil |
| 34⁽¹⁾ | 2-(CH₃-(CH₂)₆-O)-C₆H₄ | 0 | Oil |

TABLE I-continued

Structure (common to both columns):

CH₂—O
  \  / R¹
   C
  /  \
CH₂—S—CH₂—NH—N=CH—N=CH (triazole-like ring)
     ↓
    (O)ₙ

| Cpd. No. | R¹ | n | m.p. (°C.) |
|---|---|---|---|
| 35 | CH₃–S(=O)₂–O–C₆H₄– | 0 | 191–193 |
| 36 | CH₃–NH–C(=O)–O–C₆H₄– | 0 | 140–142 |
| 37⁽¹⁾ | C₆H₄–NH₂ | 0 | Oil |
| 38⁽¹⁾ | C₆H₄–N(CH₃)₂ | 0 | Oil |
| 39⁽¹⁾ | C₆H₄–N(CH₂–CH₃)₂ | 0 | Oil |
| 40 | C₆H₄–NH₂ | 0 | 105–108 |
| 41 | C₆H₄–N(CH₃)₂ | 0 | 87–89 |
| 42⁽¹⁾ | C₆H₄–N(CH₂–CH₃)₂ | 0 | Oil |
| 43 | C₆H₄–N=CH–C₆H₅ | 0 | 97–99 |
| 44 | C₆H₄–NH–C(=O)–C₆H₅ | 0 | 119–123 |
| 45 | " | 1 | 162–165 |
| 46 | C₆H₄–NH–C(=O)–O–(CH₂)₃–CH₃ | 0 | 96–97 |
| 47 | " | 2 | 141–143 |
| 48⁽¹⁾ | C₆H₄–NH–S(=O)₂–C₆H₅ | 0 | Oil |
| 49 | C₆H₄–NH–S(=O)₂–CH₃ | 0 | 188–190 |
| 50 | C₆H₄–NH–C(=O)–O–CH₂–CH₃ | 0 | 126–128 |
| 51 | C₆H₄–NH–C(=O)–O–(CH₂)₃–CH₃ | 0 | 136–137 |
| 52 | " | 1 | 154–156 |
| 53 | " | 2 | 157–159 |
| 54 | naphthyl | 0 | 80–82 |
| 55 | " | 1 | 125–130 |
| 56 | " | 2 | 149–154 |
| 57 | tetrahydrothiopyranyl (S-containing 6-ring) | 0 | 96–98 |
| 58 | " | 2 | 128–132 |
| 59 | See Table II | | |
| 60 | " | | |
| 61 | CH₃–O–C₆H₄– (Methiodide Salt) | 0 | 196–199 |
| 62 | thienyl (S) | 0 | 61–63 |
| 63 | " | 2 | 116–120 |
| 64 | 2-bromo-thienyl (S—Br) | 0 | 85–87 |
| 65 | " | 2 | 140–142 |

TABLE I-continued
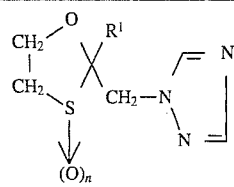
| Cpd. No. | R¹ | n | m.p. (°C.) |
|---|---|---|---|
| 66 | 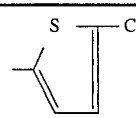 | 0 | 66–70 |
| 67 | " | 2 | 132–136 |
| 68 | 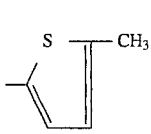 | 0 | 88–90 |
| 69 | " | 2 | 120–124 |
| 70–73 | See Table II | | |
| 74 | 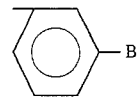 | 0 | 75–80 |
| 75 | 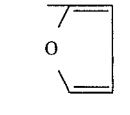 | 0 | oil |
| 76 | 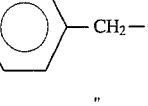 | 1 | 104–106 |
| 77 | " | 2 | 90–92 |
| 78 | 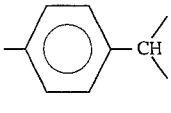 | 1 | 108–111 |
| 79 | " | 2 | 112–118 |
| 80 | 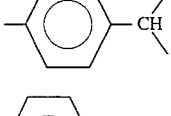 | 0 | 45–46 |
| 81[(1)] | 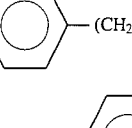 | 0 | Oil |
TABLE I-continued
| Cpd. No. | R¹ | n | m.p. (°C.) |
|---|---|---|---|
| 82 | 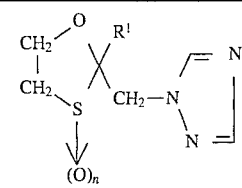 | 0 | 73–75 |
| 83 | 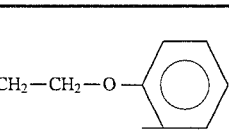 | 0 | 60–62 |
| 84 | 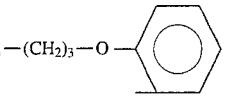 | 0 | 133–135 |
| 85 | 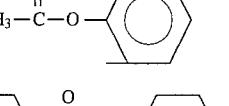 | 0 | 85–88 |
| 86 |  | 0 | 45–47 |
| 87 | 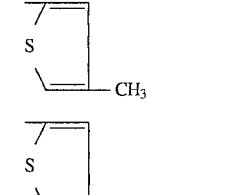 (p-toluenesulfonic acid salt) | 0 | 131–133 |
| 88[(1)] | 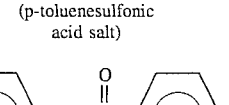 | 0 | Oil |
| 89[(1)] | 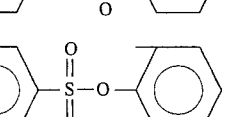 | 0 | Oil |
| 90 | 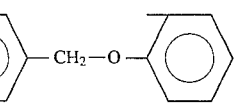 | 0 | 109–110 |

TABLE II

| Cpd. No. | R¹ | R | Y | n | m.p. (°C.) |
|---|---|---|---|---|---|
| 59 | –C₆H₄–Cl | –CH(CH₃)–CH₂– | N | 0 | 70–76 |
| 60 | " | " | " | 2 | 175–177 |
| 70 | –C₆H₅ | –CH₂–CH₂– | CH | 0 | 67–70 |
| 71 | " | " | " | 1 | 125–129 |
| 72 | –C₆H₄–Cl | " | " | 0 | 88–90 |
| 73 | " | " | " | 1 | 175–180 |

(1) Nuclear Magnetic Resonance (n.m.r.) data,:

| | |
|---|---|
| Cpd. No. 27 | (deuterated chloroform, CDCl₃): 8.0(1H, s) 7.8(1H, s), 7.3(2H, d), 6.8(2H, d), 4.7(2H, s), 4.1–4.5(2H, m), 3.9(2H, t), 2.8–3.1(2H, m), 0.7–2.1(9H, m). |
| Cpd. No. 33 | (CDCl₃): 7.7(2H, bs), 6.7–7.4(4H, m), 5.4(1H, d), 4.8(1H, d), 3.7–4.7 (4H, m), 3.2(2H, t), 0.7–2.2(9H, m). |
| Cpd. No. 34 | (CDCl₃): 7.9(1H, s), 7.7(1H, s), 6.7–7.4(4H, m), 4.8(2H, s), 3.8–4.6(2H, m), 2.5–2.9(2H, m), 0.7–2.1(13H, m). |
| Cpd. No. 37 | (CDCl₃): 8.0(1H, s), 7.8(1H, s), 6.4–7.4(4H, m), 4.6(2H, s), 3.8–4.5(2H, m), 3.7(2H, bs), 2.6–3.1(2H, m). |
| Cpd. No. 38 | (CDCl₃): 8.0(1H, s), 7.8(1H, s), 6.4–7.4(4H, m), 4.7(2H, s), 3.6–4.5(2H, m), 2.9(6H, s), 2.6–2.9(2H, m). |
| Cpd. No. 39 | (CDCl₃): 8.0(1H, s), 7.8(1H, s), 6.4–7.3(4H, m), 4.7(2H, s), 3.7–4.5(2H, m), 3.3(4H, q), 2.9(2H, m), 1.2(6H, t). |
| Cpd. No. 42 | (CDCl₃): 8.0(1H, s), 7.9(1H, s), 7.2(2H, d), 6.6(2H, d), 4.6(2H, s), 3.7–4.5(2H, m), 3.3(4H, q), 2.8–3.1(2H, m), 1.1(6H, t). |
| Cpd. No. 48 | (CDCl₃): 8.6(1H, 6s), 6.9–8.0(11H, m), 4.7(2H, s), 3.7–4.5(2H, m), 2.7–3.1(2H, m). |
| Cpd. No. 75 | (CDCl₃): 2.68–3.31(2H, m), 3.82–4.68(2H, m), 4.89(2H, s), 6.33(2H, m), 7.46(1H, m), 7.86(1H, s), 8.08(1H, s). |
| Cpd. No. 81 | (CDCl₃): 8.0(1H, s), 7.8(1H, s), 6.8–7.4(4H, m), 4.8(2H, s), 3.8–4.6(2H, m), 3.9(3H, s), 2.7–3.0(2H, m). |
| Cpd. No. 88 | (CDCl₃): 7.9(1H, s), 7.8(1H, s), 6.7–7.9.(9H, m), 4.5(2H, s), 3.6–4.4(2H, m), 2.7–3.0(2H, m). |
| Cpd. No. 89 | (CDCl₃): 7.9(1H, s), 7.7(1H, s), |

TABLE II-continued 7.0–8.3(9H, m), 4.7(2H, s),
3.7–4.6(2H, m), 2.6–2.9(2H, m).

Typical of additional compounds considered to be within the scope of this invention are listed in Table III below.

TABLE III

| Cpd. No. | R | R¹ | R² |
|---|---|---|---|
| 91 | —CH(CH₃)—CH(CH₃)— | Cl-pyridin-4-yl | H |
| 92 | —CH(n-C₄H₉)—CH₂— | CH₃-naphthyl | H |
| 93 | —CH(n-C₉—H₁₉)CH₂CH₂— | CH₃—(CH₂)₉—phenyl— | H |
| 94 | —CH₂—CH₂— | cyclohexyl-S-phenyl— | CH₃ |
| 95 | " | —phenyl—SH | H |
| 96 | " | CH₃—(CH₂)₉—S—phenyl— | H |
| 97 | " | phenyl—CH₂—S(=O)₂—phenyl— | H |
| 98 | " | phenyl—C(CH₃)₂—O—phenyl— | H |
| 99 | —CH₂—CH₂— | phenyl—NH—C(=O)—O—phenyl— | H |

TABLE III-continued $$R\underset{S}{\overset{O}{\diagdown}}\overset{R^1}{\underset{R^2}{\diagup}}CH-N\underset{N}{\overset{N}{\diagdown}}$$

| Cpd. No. | R | R¹ | R² |
|---|---|---|---|
| 100 | " | CH₃—(CH₂)₃\N—C(=O)—O—C₆H₄— / CH₃—(CH₂)₃ | H |
| 101 | " | CH₃—(CH₂)₃\N—C₆H₄— / CH₃—(CH₂)₃ | H |
| 102 | " | (tetrahydrothiophene)S⟩—N—C₆H₄— | H |
| 103 | " | CH₃—CH(CH₂—)—O—CH(CH₃)—CH₂—N—C₆H₄— (morpholine with 2,6-dimethyl) | H |
| 104 | " | Bicyclo[2.2.1]hept-5-en-2-yl | H |

EXAMPLE 7

POWDERY MILDEW SYSTEMIC CONTROL TEST

The following procedure was used to evaluate the chemicals of this invention for effectiveness in preventing or controlling the Powdery Mildew disease of barley (*Erysiphe graminis*) and cucumber Powdery Mildew (*Erysiphe cichoracearum*) by systemic root uptake; BMS and CMS respectively. Barley and cucumber plants in pots measuring 4×4× 3.5 inches and containing several plants each were grown to age 6 days and 10 days respectively, to bring them to a growth stage suitable for testing. The varieties used were "Herta" barley and "Marketmore 70" cucumber.

Chemicals for drenching the potted plants were prepared by dissolving the technical chemical in 5 to 7 ml of acetone or other suitable solvent, adding 1–2 drops of an emulsifying agent such as Triton X-100 (trademark), and emulsifying the chemical in a quantity of water to give a concentration of 250 ppm of active ingredient. For each treatment, a 45 ml quantity of solution was added to the soil in which the plants were growing. This is an amount which will saturate the soil without losing significant amounts of the chemical solution through drainage into the saucers below.

Twenty-four hours after treatment, both cucumber and barley plants were inoculated by brushing leaves from infected barley or cucumber plants on each of the treated plants and untreated controls. Six days after inoculation, disease control was evaluated on a 0–6 rating scale, with 0 equal to no disease present and 6 being severe disease. Percent control is computed by comparing the treatment ratings with that of untreated control plants.

The data are shown in Table IV.

EXAMPLE 8

The following example illustrates the usefulness of the chemicals of this invention for controlling bean powdery mildew (*E. polygoni*) and barley powdery mildew (*E. graminis*) by foliar application; BEF and BAF respectively. The procedures are as follows:

Bean Mildew

Pinto bean plants, at the primary leaf stage of growth, were sprayed with the chemicals of the invention, at a dosage of 1000 ppm. Plants were then placed in the greenhouse at 70° F. and inoculated with the *Erysiphe polygoni* spores by brushing the first and second trifoliate leaves with previously infected bean leaves covered with spores. The disease developed on untreated controls in 4–6 days. This test measures the ability of the chemical to be translocated systemically from the primary to the trifoliate leaves to provide disease control.

Barley Mildew

Seven day old barley plants were sprayed with the chemicals of the invention and were allowed to dry. The leaves of these plants were then inoculated with *Erysiphe graminis* mildew spores by brushing them with previously infected leaves which were covered with spores. The plants were then kept in the greenhouse at 70° F. for 5 days to allow disease development.

Control of disease was assessed by comparing treated plants with non-treated controls for percent of disease reduction or control. The results are shown in Table IV.

EXAMPLE 9

This concerns laboratory tests for evaluating the fungitoxicity of chemicals to various *Phytophthora infestans* (PHY) and *Botrytis cinerea* (BOT).

The candidate chemicals were solubilized in acetone at a concentration of 500 ppm. Antibiotic testing discs (11 millimeters) were dipped in the chemical test solutions, then were allowed to dry to remove the acetone solvent.

The treated discs were then placed on agar plates, and the test organisms were added to the center of each paper disc in the form of a culture plug with the fungus mat in contact with the treated paper. The plates were incubated and then evaluated by measuring the diameter of the fungus colony on the treated discs vs. that on untreated discs. Percent inhibition of growth was calculated and data from such tests appears in Table IV below.

TABLE IV

| | (% Control at (ppm)) | | | | | |
|---|---|---|---|---|---|---|
| Cpd No. | PHY (500) | BOT (500) | BEF (1000) | BAF (1000) | BMS (250) | CMS (250) |
| 1 | 80 | 70 | 85 | NT | 100 | 100 |
| 2 | 0 | 10 | NT | 100 | 100 | 100 |
| 3 | NT | 45 | 100 | NT | 100 | 100 |
| 4 | 85 | 100 | 100 | 100 | 100 | 100 |
| 5 | 15 | 50 | 100 | 100 | 100 | 100 |
| 6 | 100 | 80 | 100 | NT | 100 | 100 |
| 7 | 0 | 10 | 0 | 100 | 100 | 100 |
| 8 | 10 | 50 | 100 | 100 | 100 | 100 |
| 9 | 100 | 100 | 100 | 100 | 100 | 100 |
| 10 | 45 | 50 | 100 | 100 | 100 | 100 |
| 11 | 95 | 100 | 100 | 100 | 100 | 100 |
| 12 | 30 | 0 | 100 | 100 | 100 | 100 |
| 13 | 90 | 100 | 90 | 100 | 100 | 100 |
| 14 | 90 | 100 | 90 | 100 | 100 | 100 |
| 15 | 40 | 0 | 0 | 85 | 0 | 0 |
| 16 | 40 | 100 | 0 | 60 | 25 | 0 |
| 17 | 45 | 100 | 0 | NT | 0 | 0 |
| 18 | 15 | 100 | 0 | 100 | 0 | 15 |
| 19 | 35 | 0 | 0 | 0 | 100 | 100 |
| 20 | 35 | 25 | 0 | 0 | 85 | 0 |
| 21 | 0 | 0 | 0 | 0 | 75 | 0 |
| 22 | 0 | 30 | 0 | NT | 100 | 100 |
| 23 | 5 | 0 | 0 | NT | 35 | 0 |
| 24 | 100 | 100 | 100 | 100 | 100 | 100 |
| 25 | 60 | 0 | 100 | 100 | 100 | 100 |
| 26 | 0 | 70 | 0 | NT | 0* | 35* |
| 27 | 85 | 100 | 80 | NT | 100 | 100 |
| 28 | 25 | 0 | 0 | 85 | 0* | 40* |
| 29 | 95 | 65 | 40 | 100 | 75* | 0* |
| 30 | | | | | | |
| 31 | | | | | | |
| 32 | 100 | 100 | 100 | 100 | 100 | 100 |
| 33 | 0 | 65 | 100 | 100 | 100 | 100 |
| 34 | 100 | 100 | 100 | 100 | 0 | 80 |
| 35 | 10 | 0 | 95 | 85 | 100 | 100 |
| 36 | 55 | 0 | 0 | 25 | 100 | 100 |
| 37 | 10 | 0 | 0 | NT | 0 | 5 |
| 38 | 100 | 0 | 0 | NT | 0 | 5 |
| 39 | 0 | 0 | 0 | NT | 0 | 30 |
| 40 | 20 | 0 | 0 | 100 | 20 | 65 |
| 41 | 50 | 15 | 100 | 50 | 0 | 30 |
| 42 | 50 | 0 | 95 | 65 | 0 | 70 |
| 43 | 15 | 0 | 0 | NT | 90 | 0 |
| 44 | 40 | 10 | 0 | NT | 0 | 0 |
| 45 | 65 | 0 | 0 | NT | 0 | 0 |
| 46 | 35 | 50 | 0 | NT | 0 | 0 |
| 47 | 55 | 0 | 0 | NT | 0 | 75 |
| 48 | 0 | 0 | 0 | 0 | 0 | 25** |
| 49 | 20 | 15 | 60 | 0 | 0 | 20 |
| 50 | 0 | 70 | 50 | NT | 100 | 100 |
| 51 | 35 | 100 | NT | 85 | 0 | 0 |
| 52 | 25 | 0 | 0 | 100 | 100 | 55 |
| 53 | 10 | 0 | 0 | 95 | 35 | 35 |
| 54 | 80 | 100 | 0 | 75 | 100 | 100 |
| 55 | 0 | 60 | 75 | 15 | 15 | 100 |
| 56 | 0 | 10 | 95 | 100 | 65 | 100 |
| 57 | 100 | 100 | 90 | 100 | 100 | 100 |
| 58 | 60 | 10 | 0 | 100 | 100 | 100 |
| 59 | 0 | 100 | 100 | 100 | 100 | 100 |
| 60 | 35 | 0 | 100 | 100 | 100 | 100 |
| 61 | | | | | | |
| 62 | 40 | 75 | 50 | 50 | 100 | 100 |
| 63 | 0 | 25 | 0 | 0 | 15 | 50 |
| 64 | 100 | 100 | 90 | 100 | 100 | 100 |
| 65 | 35 | 0 | 0 | 100 | 90 | 100 |
| 66 | 100 | 100 | 100 | 100 | 100 | 100 |
| 67 | 0 | 0 | 95 | 20 | 100 | 100 |
| 68 | 55 | 20 | 75 | 70 | 80 | 100 |
| 69 | 15 | 0 | 0 | 0 | 30 | 30 |
| 70 | 100 | 85 | 95 | 100 | 85 | 100 |
| 71 | 0 | 0 | 100 | 60 | 0 | 70 |
| 72 | 100 | 95 | 50 | 90 | 100 | 100 |
| 73 | 50 | 50 | 100 | 85 | 90 | 100 |

Remarks:
*Tested at 500 ppm
**Tested on Helminthosporium at 500 ppm

The following are the preferred fungicidally active compounds of this invention:

| | |
|---|---|
| Cmpd 9: | 1H-1,2,4-triazole, 1-[[2-(4-bromophenyl)-1,3-oxathiolan-2-yl]methyl]; 1H-1,3-imidazole, 1-[[2-(4-bromophenyl)-1,3-oxathiolan-2-yl]methyl]; |
| Cmpd 24: | 1H-1,2,4-triazole, 1-[[2-[4-(1-methylethoxy)-phenyl]-1,3-oxathiolan-2-yl]methyl]; 1H-1,3-imidazole, 1-[[2-[4-(1-methylethoxy)phenyl]-1,3-oxathiolan-2-yl]methyl]; |
| Cmpd 32: | 1H-1,2,4-triazole, 1-[[2-[2-(pentyloxy)phenyl]-1,3-oxathiolan-2-yl]methyl]; 1H-1,3-imidazole, 1-[[2-[2-(pentyloxy)phenyl]-1,3-oxathiolan-2-yl]methyl]; |
| Cmpd 27: | 1H-1,2,4-triazole, 1-[[2-[4-(pentyloxy)phenyl]-1,3-oxathiolan-2-yl]methyl]; 1H-1,3-imidazole, 1-[[2-[4-(pentyloxy)phenyl]-1,3-oxathiolan-2-yl]methyl]; |
| Cmpd 72: | 1H-1,3-imidazole, 1-[[2-(4-chlorophenyl)-1,3-oxathiolan-2-yl]methyl; |
| Cmpd 4: | 1H-1,2,4-triazole, 1-[[2-(4-fluorophenyl)-1,3-oxathiolan-2-yl]methyl; 1H-1,3-imidazole, 1-[[2-(4-fluorophenyl)-1,3-oxathiolan-2-yl]methyl; |
| Cmpd 59: | 1H-1,2,4-triazole, 1-[[2-(4-chlorophenyl)-5-methyl-1,3-oxathiolan-2-yl]methyl; 1H-1,3-imidazole, 1-[(2-(4-chlorophenyl)-5-methyl-1,3-oxathiolan-2-yl]methyl; |
| Cmpd 66: | 1H-1,2,4-triazole, 1-[[2-(5-chloro-2-thienyl)-1,3-oxathiolan-2-yl]methyl; 1H-1,3-imidazole, 1-[[2-(5-chloro-2-thienyl)-1,3-oxathiolan-2-yl]methyl; |
| Cmpd 64: | 1H-1,2,4-triazole, 1-[[2-(5-bromo-2-thienyl)-1,3-oxathiolan-2-yl]methyl; 1H-1,3-imidazole, 1-[[2-(5-bromo-2-thienyl)-1,3-oxathiolan-2-yl]methyl. |

The most preferred fungicidally active compounds are:

| | |
|---|---|
| Cmpd 9: | 1H-1,2,4-triazole, 1-[[2-(4-bromophenyl)-1,3-oxathiolan-2-yl]methyl; 1H-1,3-imidazole, 1-[[2-(4-bromophenyl)-1,3-oxathiolan-2-yl]methyl; |
| Cmpd 32: | 1H-1,2,4-triazole, 1-[[2-(2-pentyloxy)phenyl]-1,3-oxathiolan-2-yl]methyl; and |

1H-1,3-imidazole, 1-[[2-(2-pentyloxy)phenyl]-1,3-oxathiolan-2-yl]methyl.

EXAMPLE 10

To illustrate the effectiveness of the described compounds as growth regulants, 600 mg of chemical were dissolved in a composition comprising 10 ml acetone to which 30 mg conventional emulsifying agent (e.g., ethoxylated sorbitan monolaurate, Tween 20 [trademark]) were added. This solution was diluted to 200 ml with distilled water, producing a 3000 ppm solution. A 1000 ppm spray solution was also made by appropriate dilution of the 3000 ppm stock solution. The spray solutions were atomized with a DeVilbiss [trademark] No. 152 sprayer, and the foliage of targeted plants was wetted to the drip point. The dosage applied to each plant species is indicated in Table V. The target plants included:

soybean, *Glycine max* (L.) Merr. cv. Williams, 2 weeks old;
cotton, *Gossypium hirsutum* L. cv. Stoneville 213, 3–4 weeks old;
bean, *Phaseolus vulgaris* L. cv. Pinto III, 2 weeks old;

After 2–3 weeks in the greenhouse, the plants were scored for retardation of vegetative growth.

TABLE V

| Cpd. No. | Growth Retardation, % (at concentration) | | |
|---|---|---|---|
| | Bean (1000 ppm) | Cotton (3000 ppm) | Soybean (3000 ppm) |
| 1 | 25 | 0 | *40 |
| 2 | 0 | 20 | 75 |
| 3 | 60 | 95 | 80 |
| 4 | 50 | 30 | 0 |
| 5 | 50 | 100 | 90 |
| 6 | 30 | 60 | 0 |
| 7 | 30 | 20 | 100 |
| 8 | 95 | 80 | 90 |
| 9 | 60 | 20 | 80 |
| 10 | 90 | 100 | 100 |
| 11 | 50 | 40 | 100 |
| 12 | 50 | 50 | 100 |
| 13 | 50 | 0 | 90 |
| 14 | 50 | 50 | 50 |
| 15 | 20 | 0 | 0 |
| 16 | 0 | 0 | 80 |
| 18 | 0 | 30 | 0 |
| 19 | 90 | 0 | 0 |
| 24 | 20 | 0 | 0 |
| 25 | 10 | 20 | 20 |
| 26 | 0 | 20 | 0 |
| 27 | 0 | 0 | 0 |
| 30 | 90 | 75 | 90 |
| 31 | 80 | 0 | 0 |
| 32 | 60 | 30 | 30 |
| 33 | 50 | 100 | 100 |
| 34 | 90 | 50 | 75 |
| 54 | 0 | 0 | 30 |
| 55 | 80 | 50 | 80 |
| 56 | 50 | 0 | 30 |
| 57 | 0 | 30 | 90 |
| 58 | 0 | 90 | 90 |
| 59 | 80 | 95 | 100 |
| 60 | 80 | 75 | 100 |
| 61 | — | — | — |
| 62 | 50 | 90 | 50 |
| 64 | 80 | 30 | 80 |
| 65 | 0 | 30 | 0 |
| 66 | 80 | 95 | 100 |
| 67 | 50 | 50 | 80 |
| 68 | 0 | 0 | 50 |

TABLE V-continued

| Cpd. No. | Growth Retardation, % (at concentration) | | |
|---|---|---|---|
| | Bean (1000 ppm) | Cotton (3000 ppm) | Soybean (3000 ppm) |
| 72 | 30 | 0 | 0 |
| 73 | 50 | 0 | 0 |
| 74 | 25 | 20 | 60 |
| 76 | 0 | 20 | 50 |
| 77 | 0 | 60 | 30 |
| 78 | 0 | 30 | 80 |
| 79 | 0 | 10 | 20 |
| 80 | 0 | 0 | 30 |
| 81 | **50 | ***100 | ***0 |
| 82 | 95 | 90 | 0 |
| 83 | **60 | ***50 | ***100 |
| 87 | 0 | 90 | 90 |
| 89 | 80 | 0 | 0 |
| 90 | 20 | 0 | 20 |

REMARKS
*Tested at 500 ppm
**Tested at 1333 ppm
***Tested at 4000 ppm

The preferred plant growth regulating compounds of this invention are the following:

| | |
|---|---|
| Cmpd 8: | 1-[[2-(4-chlorophenyl)-1,3-oxathiolan-2-yl]methyl]-1H-1,2,4-triazole S,S-dioxide; |
| Cmpd 5: | 1-[[2-(4-fluorophenyl)-1,3-oxathiolan-2-yl]methyl]-1H-1,2,4-triazole S,S-dioxide; |
| Cmpd 10: | 1-[[2-(4-bromophenyl)-1,3-oxathiolan-2-yl]methyl]-1H-1,2,4-triazole S,S-dioxide; |
| Cmpd 30: | 1-[[2-(2-ethoxyphenyl)-1,3-oxathiolan-2-yl]methyl]-1H-1,2,4-triazole; |
| Cmpd 33: | 1-[[2-(2-pentyloxyphenyl)-1,3-oxathiolan-2-yl]methyl]-1H-1,2,4-triazole S,S-dioxide; |
| Cmpd 59: | 1-[[2-(4-chlorophenyl)-5-methyl-1,3-oxathiolan-2-yl]methyl]-1H-1,2,4-triazole; |
| Cmpd 60: | 1-[[2-(4-chlorophenyl)-5-methyl-1,3-oxathiolan-2-yl]methyl]-1H-1,2,4-triazole S,S-dioxide; and |
| Cmpd 66: | 1-[[2-(5-chloro-2-thienyl)-1,3-oxathiolan-2-yl]methyl]-1H-1,2,4-triazole. |

EXAMPLE 11

Compound No. 1 was evaluated as a fungicide in comparison to the chemical 1-[(2-phenyl-1,3-dithiolan-2-yl)methyl]-1H-1,2,4-triazole (within the disclosure of EPO 61789) following essentially the procedures of Examples 7, 8 and 9, respectively. Whereas both chemicals exhibited essentially the same activity against certain fungi (*Sclerotium rolfsii, Fusarium oxysporum, Cercospora arachidicola* and *phytophthora infestans*) the compound of this invention far exceeded the fungicidal efficacy of the prior art chemical against the majority of fungi tested. For results, see Table VI.

TABLE VI

| Fungicidal Control, %, Comparison | | | | |
|---|---|---|---|---|
| Test Fungus | | at ppm | Cpd. 1 | Prior Art (dithiolane) |
| ALT | (1) | 500 | 35 | 0 |
| BARBEST | (2) | 1000 | 10 | 100 |
| BMS | (3) | 62 | 100 | 66 |
| | | 31 | NT | 17 |
| | | 12 | 100 | NT |
| BOT | (4) | 500 | 70 | 0 |
| BRED | (5) | 100 | 50 | 80 |

TABLE VI-continued

Fungicidal Control, %, Comparison

| Test Fungus | | at ppm | Cpd. 1 | Prior Art (dithiolane) |
|---|---|---|---|---|
| CERC | (6) | 500 | + | + |
| CMS | (7) | 250 | 100 | 0 |
| | | 12 | 100 | NT |
| FUS | (8) | 500 | 65 | 65 |
| H-MAY | (9) | 500 | 35 | 65 |
| PHYTOF | (10) | 20 | 33 | 41 |
| PMPRO | (11) | 1000 | 85 | 0 |
| SCLERM | (12) | 500 | 25 | 25 |
| SCLERO | (13) | 500 | 35 | 0 |

Remarks: (1) *Alternaria solani*
(2) Barley Blast
(3) Barley Mildew, systemic
(4) *Botrytis cenerea*
(5) Bean rust eradicant
(6) *Cercospora*
(7) Cucumber mildew, systemic
(8) *Fusarium*
(9) *Helminthosporium maydis*
(10) *Phytophthora*
(11) Barley powdery mildew protectant
(12) *Sclerotium*
(13) *Sclerotinia*
NT Not tested at that concentration

EXAMPLE 12

Compound No. 6 was evaluated as a fungicide in comparison to the chemical 1-[(2-(4-chlorophenyl)-1,3-dioxolan-2-yl)methyl]-1H-1,2,4-triazole (within the disclosure of U.S. Pat. No. 4,160,838) following essentially the procedures of Examples 7, 8 and 9, respectively. Whereas both chemicals exhibited essentially the same activity against certain fungi (barley mildew, bean rust eradicant, cucumber mildew and sclerotium) the compound of this invention far exceeded the fungicidal efficacy of the prior art chemical against the majority of fungi tested. For results, see Table VII.

TABLE VII

Fungicidal Control, %, Comparison

| Test Fungus | at ppm | Cpd. 6 | Prior Art (dioxolane) |
|---|---|---|---|
| ALT | 500 | 45 | 0 |
| BARBEST | 100 | 100 | 35 |
| BMS | 62 | 100 | 100 |
| BOT | 500 | 80 | 35 |
| BRED | 1000 | 100 | 100 |
| CERC | 500 | + | — |
| CMS | 250 | 100 | 100 |
| FUS | 500 | 80 | 50 |
| H-MAY | 500 | 100 | 35 |
| PHYTOF | 20 | 100 | 65 |
| PMPRO | 1000 | 100 | 0 |
| SCLERM | 500 | 50 | 65 |
| SCLERO | 500 | 55 | 0 |

Although the invention has been illustrated by the preceding examples, it is not to be construed as being limited to those embodiments, but rather, the invention encompasses the generic area as hereinbefore disclosed. Various modifications and embodiments can be made without departing from the spirit and scope thereof.

We claim:

1. A compound of the formula:

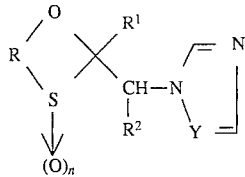

wherein

R is $C_2$–$C_4$ alkylene unsubstituted or substituted with $C_1$–$C_{10}$ alkyl, alkenyl, alkynyl or alkoxyalkyl;

$R^1$ is
(a) $C_5$–$C_8$ bridged or non-bridged cycloalkyl or cycloalkenyl;
(b) phenyl, methylenedioxyphenyl, pyridyl, furanyl or thienyl; the (b) substituents being unsubstituted or substituted with:
$C_1$–$C_{10}$ alkyl, OH, SH, cyclohexyl, $C_1$–$C_{10}$ haloalkyl, $C_1$–$C_{10}$ alkenyl, cyano, nitro, $XR^3$ or a single halogen
wherein X is O, S, SO or $SO_2$ and $R^3$ is $C_1$–$C_{10}$ alkyl, $C_1$–$C_{10}$ alkenyl, $C_1$–$C_{10}$ alkoxyalkyl, $C_1$–$C_6$ haloalkyl, $C_1$–$C_6$ haloalkenyl, $C_5$–$C_6$ cycloalkyl, $C_7$–$C_9$ aralkyl;
$C_1$–$C_4$ alkylsulfonyloxy, phenylsulfonyloxy,

wherein $R^4$ is $C_1$–$C_4$ alkyl or phenyl;

wherein $R^5$ and $R^6$ are individually H, $C_1$–$C_4$ alkyl or phenyl with the proviso that $R^5$ and $R^6$ are not both H;
$NR^7R^8$
wherein $R^7$ and $R^8$ are individually H or $C_1$–$C_4$ alkyl, $R^7$ is H, $R^8$ is $COR^9$, $COOR^9$ or $SO_2R^9$
wherein $R^9$ is $C_1$–$C_4$ alkyl or phenyl, or $R^7$ and $R^8$ together form $C_4$–$C_6$ alkylene, $C_4$–$C_6$ oxydialkylene or phenylmethylene;

$R^2$ is H or $C_1$–$C_6$ alkyl;

Y is CH; and n is 0, 1 or 2; and the physiologically acceptable addition salts thereof.

2. A compound according to claim 1 wherein:

R is $C_2$ alkylene unsubstituted or substituted with $C_1$–$C_3$ alkyl;

$R^1$ is
(a) $C_5$–$C_6$ cycloalkyl;
(b) unsubstituted phenyl, thienyl; phenyl or thienyl substituted with F, Cl, Br, $C_1$–$C_7$ alkyl, $XR^3$
wherein X is O, S, SO or $SO_2$ and $R^3$ is $C_1$–$C_7$ alkyl, cyclohexyl; methylsulfonyloxy, phenylsulfonyloxy, dimethylaminocarbonyloxy or $NR^7R^8$
wherein $R^7$ and $R^8$ are individually H or $C_1$–$C_2$ alkyl $R^7$ and $R^8$ together are phenylmethylene and
where $R^7$ is H, $R^8$ is methylsulfonyl, phenylsulfonyl or $C_1$–$C_4$ alkyoxycarbonyl;

$R^2$ is H;

Y is CH; and n is 0, 1 or 2.

3. A compound according to claim 1 wherein:

R is $C_2$ alkylene unsubstituted or substituted with $C_1$–$C_3$ alkyl;

$R^1$ is
 (a) cyclohexyl;
 (b) unsubstituted phenyl, thienyl; phenyl or thienyl substituted with F, Cl, Br, $C_1$–$C_7$ alkyl or $C_2$–$C_7$ alkoxy;

$R^2$ is H; and n is 0, 1 or 2.

4. A compound according to claim 1 wherein:

R is $C_2$ alkylene unsubstituted or substituted with $C_1$–$C_3$ alkyl;

$R^1$ is
 (a) cyclohexyl;
 (b) phenyl or thienyl substituted with F, Cl, Br, $C_1$–$C_7$ alkyl or $C_2$–$C_7$ alkoxy;

$R^2$ is H;

Y is CH; and n is 0, 1 or 2.

5. A compound according to claim 1 wherein compound of Formula (I) is selected from the group consisting of 1H-1,3-imidazole, 1-[[2-(4-bromophenyl)-1,3-oxathiolan-2-yl]methyl]; 1H-1,3-imidazole, 1-[[2-[4-(1-methylethoxy)phenyl]-1,3-oxathiolan-2-yl]methyl]; 1H-1,3-imidazole, 1-[[(pentyloxy)phenyl] -1,-1,3-oxathiolan-2-yl ] methyl]; 1H-1,3-imidazole, 1-[ 2-[4-(pentyloxy)phenyl]-1,3-oxathiolan -2-yl]methyl]; 1H-1,3-imidazole, 1-[[2-4-chlorophenyl) -1,3-oxathiolan-2-yl]methyl; 1H-1,3-imidazole, 1-[[2-( 4-fluorophenyl)-1,3-oxathiolan-2-yl]methyl]; 1H-1,3-imidazole, 1-[[2-(4-chlorophenyl)-5-methyl-1 oxathiolan-2-yl]methyl; 1H-1,3-imidazole, 1H-1,3-imidazole, 1-[[2-(bromo-2-thienyl) -1,3-oxathiolan-2-yl]methyl.

6. A fungicidal composition comprising an inert carrier and, as the active ingredient, a fungicidally effective amount of a compound of claim 1.

7. A fungicidal composition comprising an inert carrier and, as the active ingredient, a fungicidally effective amount of a compound of claim 2.

8. A fungicidal composition comprising an inert carrier and, as the active ingredient, a fungicidally effective amount of a compound of claim 3.

9. A fungicidal composition comprising an inert carrier and, as the active ingredient, a fungicidally effective amount of a compound of claim 4.

10. A fungicidal composition comprising an inert carrier and, as the active ingredient, a fungicidally effective amount of a compound of claim 5.

11. A method of protecting crops from fungicidal attack which comprises treating said crops with an effective amount of a compound of claim 1.

12. A method of protecting crops from fungicidal attack which comprises treating said crops with an effective amount of a compound of claim 2.

13. A method of protecting crops from fungicidal attack which comprises treating said crops with an effective amount of a compound of claim 3.

14. A method of protecting crops from fungicidal attack which comprises treating said crops with an effective amount of a compound of claim 4.

* * * * *